United States Patent
Chang et al.

(10) Patent No.: US 10,765,720 B2
(45) Date of Patent: Sep. 8, 2020

(54) COMPOSITION FOR PREVENTING OR TREATING HYPEROXIA-INDUCED LUNG INJURY COMPRISING WKYMVM PEPTIDE AS AN ACTIVE INGREDIENT

(71) Applicants: SAMSUNG LIFE PUBLIC WELFARE FOUNDATION, Seoul (KR); PUSAN NATIONAL UNIVERSITY INDUSTRY-UNIVERSITY COOPERATION FOUNDATION, Busan (KR)

(72) Inventors: Yun Sil Chang, Seoul (KR); Won Soon Park, Seoul (KR); So Yoon Ahn, Seoul (KR); Dong Kyung Sung, Seoul (KR); Young Eun Kim, Gyeonggi-do (KR); Jae Ho Kim, Busan (KR)

(73) Assignees: SAMSUNG LIFE PUBLIC WELFARE FOUNDATION, Seoul (KR); PUSAN NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 0 days.

(21) Appl. No.: 16/207,441

(22) Filed: Dec. 3, 2018

(65) Prior Publication Data

US 2019/0192613 A1 Jun. 27, 2019

(30) Foreign Application Priority Data

Dec. 4, 2017 (KR) .................. 10-2017-0164880

(51) Int. Cl.
| | |
|---|---|
| *A61K 38/08* | (2019.01) |
| *A61K 38/00* | (2006.01) |
| *C07K 7/06* | (2006.01) |
| *C07K 7/00* | (2006.01) |
| *A61P 11/00* | (2006.01) |
| *A61P 29/00* | (2006.01) |

(52) U.S. Cl.
CPC .............. *A61K 38/08* (2013.01); *A61P 11/00* (2018.01); *A61P 29/00* (2018.01)

(58) Field of Classification Search
CPC .......... A61K 38/08; A61K 38/00; C07K 7/06; C07K 7/00; A61P 11/00; A61P 29/00

USPC .................. 514/1.1, 21.8; 530/300, 329
See application file for complete search history.

(56) References Cited

U.S. PATENT DOCUMENTS 8,697,635 B2 * 4/2014 Kim ................ A61K 9/0043
514/2.3

FOREIGN PATENT DOCUMENTS

KR 10-2010-0123240 A 11/2010

OTHER PUBLICATIONS

Asogingh et al, "Endothelial Colony-Forming Cells in Pulmonary Arterial Hypertension," Lung Stem Cells in the Epithelium and Vasculature, Springer, pp. 183-192. (Year: 2015).*
Kim, Y. E., et al.; "WKYMVm, formyl peptide receptor (FPR) 2 agonists, improved neonatal hyperoxic lung injury by promoting angiogenesis", Poster by Samsung Medical Center and Sung Kyun Kwan University, May 9, 2017.
Martin, C. R., et al.; "ResolvinD1 and Lipoxin A4 Improve Alveolarization and Normalize Septal Wall Thickness in a Neonatal Murine Model of Hyperoxia-Induced Lung Injury", PLOS ONE, Jun. 2014, vol. 9, Issue 6, pp. 1-9.
Cattaneo, F., et al.; "Distinct Signaling Cascades Elicited by Different Formyl Peptide Receptor 2 (FPR2) Agonists", International Journal of Molecular Sciences, 2013, 14, pp. 7193-7230.
Alphonse, R. S., et al.: "Existence, Functional Impairment, and Lung Repair Potential of Endothelial Colony-Forming Cells in Oxygen-Induced Arrested Alvolar Growth", Vascular Medicine, 2014, pp. 2144-2157.
Choi, Y. H., et al.; "Biomedical therapy using synthetic WKYMVm hexapeptide", Organogenesis, 12:2, 2016, pp. 53-60.
Office Action from corresponding Korean Patent Application No. 10-2017-0164880, dated Mar. 7, 2019.

* cited by examiner

*Primary Examiner* — Julie Ha
(74) *Attorney, Agent, or Firm* — Harness, Dickey & Pierce, P.L.C.

(57) ABSTRACT

A composition for alleviating, preventing, or treating hyperoxia-induced lung injury, the composition including the WKYMVm peptide as an active ingredient is described. The composition has an effect of increasing FPR2 activation and ERK phosphorylation, and also has an effect of improving alveolarization and angiogenesis in hyperoxia-induced lung injury models, and thus the composition is anticipated to be usefully used for the alleviation, prevention, or treatment of hyperoxia-induced lung injury, particularly bronchopulmonary dysplasia.

10 Claims, 11 Drawing Sheets

Specification includes a Sequence Listing.

COMPOSITION FOR PREVENTING OR TREATING HYPEROXIA-INDUCED LUNG INJURY COMPRISING WKYMVM PEPTIDE AS AN ACTIVE INGREDIENT

CROSS-REFERENCE TO RELATED APPLICATION

This application claims priority to and the benefit of Korean Patent Application No. 10-2017-0164880, filed on Dec. 4, 2017, the disclosure of which is incorporated herein by reference in its entirety.

FIELD

The present disclosure relates to a composition for treating hyperoxia-induced lung injury, and more particularly, to a composition for preventing, treating, or alleviating hyperoxia-induced lung injury, which include the WKYMVm (SEQ ID NO: 1) peptide as an active ingredient.

BACKGROUND

Bronchopulmonary dysplasia (BPD) is a multifactorial chronic lung disease that occurs as a major complication of premature infants due to prolonged mechanical ventilation, the main features of bronchopulmonary dysplasia are increased inflammation, the inhibition of angiogenesis, damaged alveoli, and the like, and bronchopulmonary dysplasia causes the high mortality rate of premature babies, but despite long studies on bronchopulmonary dysplasia, it is impossible to treat bronchopulmonary dysplasia.

Formyl-peptide receptor type 2 (FPR2), which is a G-protein coupled receptor, is known to be expressed in various types of cells. The earliest discovered functions of FPR2 include inflammation control in immune cells such as white blood cells and various contributions to cellular metabolism. FPR2 is known to not only perform anti-inflammatory functions, but also mediate cell proliferation, migration, and angiogenesis in endothelial cells. FPR2 activation is known to increase cytoplasmic calcium levels that induce cell signaling, such as the ERK pathway, and to increase chemotaxis, cell proliferation, and angiogenesis in order to maintain tissue homeostasis in damaged tissues in a manner dependent on specific cell types and microenvironment.

Meanwhile, WKYMVm (Trp-Lys-Tyr-Met-Val-D-Met, a synthetic peptide) (SEQ ID NO: 1), which is a synthetic peptide identified by screening peptide libraries, is known as a potent agonist of FPR2 that activates leukocytes. In previous studies, it was confirmed that WKYMVm (SEQ ID NO: 1) increased cell survival and migration through FPR2, and increased angiogenesis in endothelial cells in vitro. In addition, in in vivo studies, it was confirmed that WKYMVm (SEQ ID NO: 1) promoted angiogenesis and tissue repair.

Previous studies have shown that lipoxin A4 and resolvin D1, which bind to FPR2, improve alveolar damage caused by bronchopulmonary dysplasia in neonatal mice (Martin C R, Zaman M M, Gilkey C, Salguero M V, Hasturk H, et al. (2014) PLoS One 9: e98773.), but an effect of WKYMVm (SEQ ID NO: 1) on lung damage due to bronchopulmonary dysplasia has not been known. In addition, the use of WKYMVm (SEQ ID NO: 1) in the treatment of hyperoxia-induced lung injury has not yet been adequately studied.

SUMMARY

The present disclosure has been made to address the above-described problems, and as a result of having conducted research on the treatment of bronchopulmonary dysplasia, the inventors of the present disclosure verified an effect of the WKYMVm (SEQ ID NO: 1) peptide on alleviating hyperoxia-induced lung damage of neonatal mice in vitro and in vivo, thus completing the present disclosure based on these findings.

An object of the present disclosure is to provide a pharmaceutical composition for preventing or treating hyperoxia-induced lung injury, which includes, as an active ingredient, the WKYMVm (SEQ ID NO: 1) peptide consisting of an amino acid sequence of Trp-Lys-Tyr-Met-Val-D-Met.

Further, another object of the present disclosure is to provide a health functional food composition for alleviating hyperoxia-induced lung injury, which includes, as an active ingredient, the WKYMVm (SEQ ID NO: 1) peptide consisting of an amino acid sequence of Trp-Lys-Tyr-Met-Val-D-Met.

However, technical problems to be achieved by the present disclosure are not limited to the above-described technical problems, and other unmentioned technical problems will become apparent from the following description to those of ordinary skill in the art.

In order to achieve the aforementioned objects, the present disclosure provides a pharmaceutical composition for preventing or treating hyperoxia-induced lung injury, including, as an active ingredient, the WKYMVm (SEQ ID NO: 1) peptide consisting of an amino acid sequence of Trp-Lys-Tyr-Met-Val-D-Met.

In one embodiment of the present disclosure, the hyperoxia-induced lung injury may be any one selected from the group consisting of bronchopulmonary dysplasia, fibrosis, and chronic obstructive pulmonary disease.

In another embodiment of the present disclosure, the hyperoxia-induced lung injury may be bronchopulmonary dysplasia.

In another embodiment of the present disclosure, the WKYMVm(SEQ ID NO: 1) peptide may activate formyl-peptide receptor type 2 (FPR2).

In another embodiment of the present disclosure, the WKYMVm (SEQ ID NO: 1) peptide may increase the phosphorylation of an extracellular signal-regulated kinase (ERK).

In another embodiment of the present disclosure, the WKYMVm (SEQ ID NO: 1) peptide may induce angiogenesis.

In another embodiment of the present disclosure, the WKYMVm (SEQ ID NO: 1) peptide may reduce inflammation.

In addition, the present disclosure provides a health functional food composition for alleviating hyperoxia-induced lung injury, including, as an active ingredient, the WKYMVm (SEQ ID NO: 1) peptide consisting of an amino acid sequence of Trp-Lys-Tyr-Met-Val-D-Met.

In addition, the present disclosure provides a method of preventing or treating hyperoxia-induced lung injury, which includes administering the above-described composition to an individual.

Further, the present disclosure provides a use of the above-described composition for preventing or treating hyperoxia-induced lung injury.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
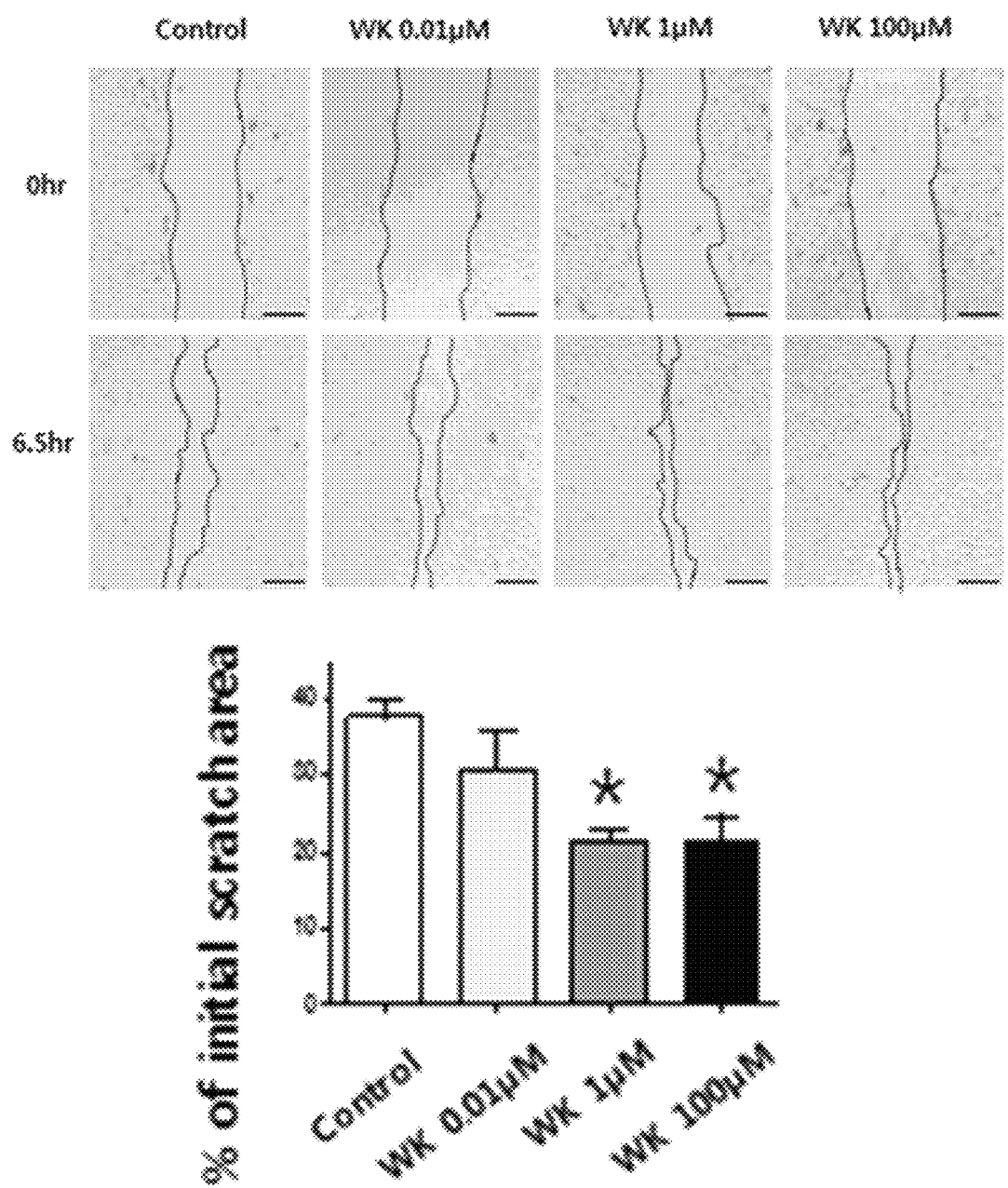
FIG. 1A illustrates analysis results of the cell proliferation of HUVECs after WKYMVm treatment according to an embodiment of the present disclosure, and results of confirming cell proliferation 6.5 hours after monolayers of HUVECs were scratched.

Exemplary embodiments of the present disclosure will be described in detail below with reference to the accompanying drawings. While the present disclosure is shown and described in connection with exemplary embodiments thereof, it will be apparent to those skilled in the art that various modifications can be made without departing from the spirit and scope of the invention.

Hereinafter, the present disclosure will be described in detail.

As a result of having studied a novel active ingredient for the treatment of hyperoxia-induced lung injury, particularly bronchopulmonary dysplasia, the inventors of the present disclosure verified that the WKYMVm(SEQ ID NO: 1) peptide had a therapeutic effect on hyperoxia-induced lung injury, particularly bronchopulmonary dysplasia by promoting angiogenesis, FPR2 activation, and ERK phosphorylation in hyperoxia-induced cells and animal models, thus completing the present disclosure.

Therefore, the present disclosure provides a pharmaceutical composition for the prevention or treatment of hyperoxia-induced lung injury, which includes the WKYMVm peptide as an active ingredient.

The WKYMVm (SEQ ID NO: 1) peptide, which is an active ingredient of the pharmaceutical composition according to the present disclosure, consists of an amino acid sequence of tryptophan (Try)-lysine (Lys)-tyrosine (Tyr)-methionine (Met)-valine (Val)-D-Met (WKYMVm), and is capable of strongly binding to formyl-peptide receptor type 2 (FPR2).

The term "prevention" as used herein means all actions that inhibit or delay the onset of hyperoxia-induced lung injury via administration of the composition of the present disclosure.

The term "treatment" as used herein means all actions that improve or beneficially change symptoms of hyperoxia-induced lung injury via administration of the composition of the present disclosure.

The term "hyperoxia-induced lung injury" as used herein refers to lung damage due to hyperoxia exposure, and the hyperoxia-induced lung injury may be any one selected from the group consisting of fibrosis, bronchopulmonary dysplasia, and chronic obstructive pulmonary disease, and is more preferably bronchopulmonary dysplasia, but the present disclosure is not limited thereto. All lung injuries caused by oxidative stress due to hyperoxia exposure are included herein.

As used herein, the term "bronchopulmonary dysplasia," which is a disease to be alleviated, prevented, or treated, refers to a chronic lung disease that occurs in patients who have undergone artificial ventilation therapy and oxygen therapy due to infant respiratory distress syndrome, and bronchopulmonary dysplasia is common in premature infants with low gestational age and low birth weight. Some extremely low birth weight infants require artificial ventilation even without infant respiratory distress syndrome, due to apnea or respiratory failure, and bronchopulmonary dysplasia may occur even in these cases. Bronchopulmonary dysplasia may generally be defined as the case of requiring oxygen supply even after a gestational age of 36 weeks, and is classified as mild, moderate, and severe depending on the degree of need for oxygen.

In one embodiment of the present disclosure, as a result of examining an angiogenic effect of WKYMVm (SEQ ID NO: 1) treatment in a randomly generated scratch area of a human umbilical vein endothelial cell (HUVEC) monolayer, it was confirmed that WKYMVm (SEQ ID NO: 1)-treated groups showed a significant increase in cell proliferation and vascular tube formation as compared to a control (non-treated group) (see Example 2). In addition, as a result of examining ERK levels by WKYMVm (SEQ ID NO: 1), it was confirmed that, although levels of total ERK were similar, the level of active ERK phosphorylation was significantly higher in the WKYMVm (SEQ ID NO: 1)-treated groups than in the control (see Example 3).

In another embodiment of the present disclosure, it was confirmed that the WKYMVm (SEQ ID NO: 1) treatment increased the levels of FPR2 expression and ERK phosphorylation in animal models (see Example 4), and as a result of having conducted mean linear intercept (MLI) and mean alveolar volume (MAV) anaylsis in order to confirm the degree of injury in lung tissues, improvement of hyperoxia-induced morphological alveolar injury upon WKYMVm (SEQ ID NO: 1) peptide treatment was particularly confirmed (see Example 5).

In addition, to histologically quantify angiogenesis and inflammation, cell detection was performed using vWF and TUNEL methods, and the results particularly confirmed that, when hyperoxia-induced lungs were treated with the WKYMVm (SEQ ID NO: 1) peptide, vWF intensity was significantly increased, the number of TUNEL-positive cells was significantly reduced, and CD68- and MPO-positive cells were significantly reduced (see Example 6).

These results suggest that the WKYMVm (SEQ ID NO: 1) peptide induces angiogenesis in hyperoxia-induced lung injury and exhibits an effect of improving the morphological damage of alveoli, and thus that it may be usefully used as a therapeutic agent of hyperoxia-induced lung injury.

The pharmaceutical composition according to the present disclosure includes the WKYMVm (SEQ ID NO: 1) peptide as an active ingredient, and may also include a pharmaceutically acceptable carrier. The pharmaceutically acceptable carrier includes, but is not limited to, saline, sterilized water, Ringer's solution, buffered saline, cyclodextrin, dextrose solution, a maltodextrin solution, glycerol, ethanol, and liposomes that are commonly used in formulation, and may further include, if needed, other general additives such as an antioxidant, a buffer solution, and the like. The pharmaceutical composition may be formulated into injectable preparations such as aqueous solutions, suspensions, emulsions, and the like, pills, capsules, granules, or tablets by additionally including a diluent, a dispersant, a surfactant, a binder, a lubricant, or the like. Suitable pharmaceutically acceptable carriers and preparations may be formulated according to respective ingredients, using methods described in Remington's reference. Preparations of the pharmaceutical composition of the present disclosure are not particularly limited, but may be formulated into injections, inhalants, agents for external application to the skin, oral ingestions, or the like.

The pharmaceutical composition of the present disclosure may be administered orally or parenterally (e.g., intravenous administration, subcutaneous administration, dermal administration, intranasal administration, or airway administration) according to the desired method. A suitable dose of the pharmaceutical composition varies according to conditions and body weight of patients, the severity of diseases, drug form, administration routes, and administration time, but may be appropriately selected by one of ordinary skill in the art.

The composition according to the present disclosure is administered in a pharmaceutically effective amount. The term "pharmaceutically effective amount" as used herein refers to an amount sufficient to treat diseases at a reasonable benefit/risk ratio applicable to medical treatment, and an effective dosage level may be determined according to factors including the type of disease of patients, the severity of disease, the activity of drugs, sensitivity to drugs, administration time, administration routes, excretion rate, treatment periods, and simultaneously used drugs, and other factors well known in the medical field. The composition according to the present disclosure may be administered as an individual therapeutic agent or in combination with other therapeutic agents, may be administered sequentially or simultaneously with conventional therapeutic agents, and may be administered in a single dosage form or multiple dosage forms. It is important to administer the composition in a minimum amount that enables a maximum effect to be obtained without side effects in consideration of all the above-described factors, and this may be easily determined by one of ordinary skill in the art.

In particular, the effective amount of the composition according to the present disclosure may vary depending on the age, gender, and body weight of patients, and may generally range from about 0.001 mg to about 150 mg, preferably about 0.01 mg to about 100 mg, per 1 kg of body weight, and the composition may be administered daily or every other day or may be administered once to three times a day. However, the effective amount may be increased or decreased depending on administration routes, the severity of diseases, gender, body weight, age, and the like, and thus the above-described dose is not intended to limit the scope of the present disclosure in any way.

Another embodiment of the present disclosure provides a health functional food composition for alleviating hyperoxia-induced lung injury, which includes the WKYMVm peptide as an active ingredient. More particularly, the composition of the present disclosure may be added to a health functional food to prevent or alleviate hyperoxia-induced lung injury, and when the composition of the present disclosure having an effect of preventing or alleviating hyperoxia-induced lung injury is used as a food additive, the composition may be used directly or in combination with other foods or food ingredients, and it may be appropriately used according to a general method. The amounts of active ingredients to be mixed may be appropriately determined according to the purpose of use (for prevention, health, or therapeutic treatment). Generally, for the preparation of foods or beverages, the active ingredient of the present disclosure is added in an amount of 15 wt % or less, preferably 10 wt % or less, with respect to a total amount of raw materials. However, in the case of long-term ingestion for health and hygienic purposes or for health care purposes, the active ingredient may be used in an amount below the range, or it may be used in an amount exceeding the range because there is no problem in terms of safety.

The type of food is not particularly limited. Non-limiting examples of foods to which the above ingredient may be added include meat, sausage, bread, chocolate, candies, snacks, confectioneries, pizza, ramen, other noodles, gums, dairy products including ice cream, various soups, beverages, tea, drinks, alcoholic beverages, and vitamin complexes, and all health functional foods in the ordinary sense are included.

A health beverage composition of the present disclosure may include additional ingredients such as various flavoring agents, natural carbohydrates, or the like as in general beverages. Examples of the above-described natural carbohydrates include monosaccharides such as glucose and fructose; disaccharides such as maltose and sucrose; polysaccharides such as dextrin and cyclodextrin, and sugar alcohols such as xylitol, sorbitol, erythritol, and the like. As a flavoring agent, a natural flavoring agent such as thaumatin or stevia extracts and a synthetic flavoring agent such as saccharin or aspartame may be used. The proportion of the natural carbohydrates generally ranges from about 0.01 g to about 0.20 g, preferably about 0.04 g to about 0.10 g, with respect to 100 ml of the composition of the present disclosure.

In addition to the above-listed ingredients, the composition of the present disclosure may include various nutritional supplements, vitamins, electrolytes, flavors, colorants, pectic acid and salts thereof, alginic acid and salts thereof, organic acids, a protective colloid thickener, a pH adjuster, a stabilizer, a preservative, glycerin, alcohols, a carbonating agent used in carbonated beverages, and the like. In addition, the composition of the present disclosure may include flesh used for the preparation of natural fruit juice, fruit juice beverages, and vegetable beverages. These ingredients may be used alone, or a combination thereof may be used. The proportion of these additives is not very important, but the amounts of the additives generally range from about 0.01 part by weight to about 0.20 part by weight with respect to 100 parts by weight of the composition of the present disclosure.

The term "alleviation" as used herein means all actions that at least reduce the parameter indicating conditions being treated, e.g., degree of symptoms.

Another embodiment of the present disclosure provides a method of preventing, controlling, or treating hyperoxia-induced lung injury, including administering the pharmaceutical composition to an individual.

The term "individual" as used herein refers to a subject with a disease requiring prevention, control, or a treatment method, and more particularly refers to mammals, e.g., humans, non-human primates, mice, rats, dogs, cats, horses, cows, and the like.

Hereinafter, exemplary examples will be described to aid in understanding of the present disclosure. However, these examples are provided only to facilitate understanding of the present disclosure and are not intended to limit the scope of the present disclosure.

EXAMPLES

Example 1

Experimental Preparation and Experimental Methods 1-1. In Vitro Cell Proliferation Analysis To confirm an angiogenic effect of the WKYMVm (SEQ ID NO: 1) peptide according to the present disclosure, a scratch wound closure assay was performed using human umbilical vein endothelial cells (HUVECs, Invitrogen, Carlsbad, CA, USA).

More particularly, HUVECs were inoculated in a 12-well plate and cultured in an M200 culture medium supplemented with low supplement growth serum (LSGS), and then when the HUVECs were saturated with a monolayer, scratches were made using a yellow pipette tip to form a wound on the HUVECs. Subsequently, the HUVECs were treated with the WKYMVm (SEQ ID NO: 1) at concentrations of 0.01 µM, 1 µM, and 100 µM (At this time, the concentrations of the WKYMVm (SEQ ID NO: 1) peptide were determined by referencing previous other reports) and incubated for 6.5 hours, and then an area covered by the HUVECs was analyzed using Image J software (National Institutes of Health, Bethesda, Md., USA).

1-2. Tube Formation Assay

A 12-well plate was coated with Matrigel Basement Membrane Matrix (Corning Inc, Corning, N.Y., USA), and then HUVECs were inoculated therein at a density of $4 \times 10^4$ cells/well, followed by culturing in a culture medium containing WKYMVm (SEQ ID NO: 1) at a concentration of 0 µM, 0.01 µM, 1 µM, or 100 µM. After incubation for 24 hours, tube networks were quantified by measuring tube length in pixel unit.

1-3. Western Blotting Analysis

To investigate whether ERK signaling is associated with downstream of the FPR2 pathway, protein levels of total ERK and phosphorylated ERK were measured by western blotting in vitro and in vivo.

More particularly, HUVECs or lung tissues were lysed using protein extraction buffer (PRO-PREP solution, iNtRON Biotechnology Inc, Seongnam, Korea), and then proteins were transferred onto a nitrocellulose membrane. Subsequently, the membrane was incubated with anti-total ERK 42/44 (1:2000; Cell Signaling Technology, Danvers, Mass., USA) and anti-pERK 42/44 (1:2000; Cell signaling Technology), and FPR2 expression levels were measured by western blotting after incubation with anti-FPR2 (1:1000; Novus Biologicals). In this case, glycerol aldehyde 3-phosphate dehydrogenase (GAPDH) was used as a loading control (1:1000; Santa Cruz Biotechnology, Santa Cruz, Calif., USA) to perform quantification. In addition, anti-rabbit Ig HRP-conjugated antibodies (1:1000; DAKO, Glostrup, Denmark) were used in a secondary antibody culture process, and an image of protein bands was acquired using an ImageQuant LAS 4000 digital imaging system (GE Healthcare).

1-4. Preparation of Hyperoxia-Induced Lung Injury Animal Models

Pregnant C57/BL6 wild-type mice (National Experimental Animal Center, Pocheon, Korea) were raised in individual cages by offering a free access to water and food to each mouse, the mice spontaneously gave birth to babies, and then the offsprings were grown in a chamber under hyperoxia (80% $O_2$) conditions (P) or normal oxygen (21% $O_2$) conditions by day 14. At this time, environmental humidity and temperature were maintained at 50% and 24° C., and to investigate the effect of activated FPR2, WKYMVm (SEQ ID NO: 1) or physiological saline (vehicle, 20 µl) was intraperitoneally administered to each mouse every day from P5 to P8. In this case, death of the animals was not observed throughout the entire experimental processes.

Meanwhile, the experimental protocol for conducting animal experiments was approved by the Animal Care and Use Committee of Samsung Life Science Research (Seoul, Korea), and all procedures were carried out in accordance with institutional guidelines and the guidelines of the health laboratory. In addition, animals used were supplied from organizations accredited by the Association for Assessment and Accreditation of Laboratory Animal Care International (AAALAC International).

1-5. Tissue Preparation

To obtain mouse lung tissues for histological evaluation, mice were sacrificed under pentobarbital anesthesia (60 mg/kg, i.p.) on P14 and subjected to myocardial perfusion using ice-cold physiological saline, and then lungs of the mice were inflated with normal saline and immersed in 10% buffered formalin as before. The fixed lung tissues were paraffin-embedded and cut into 4 µm sections.

1-6. Pulmonary Morphometry

The extent of alveolarization was determined by MLI, which describes the mean intra-alveolar distance as described by Cooney and Thurlbeck, using H&E-stained lung sections. Information on the detailed MLI measurement method was obtained by referencing conventional documents.

1-7. Immunohistochemistry

To detect FPR2 expressed in HUVECs, FPR2 was stained with anti-FPR2 antibodies (1:50, Novus Biologicals, Littleton, Colo., USA) and anti-rabbit IgG secondary antibodies (1:500; Invitrogen, Eugene, Oreg., USA).

In addition, to histologically quantify angiogenesis and inflammation, endothelial cells were stained with anti-vWF (anti-von Willebrand factor) antibodies (1:250, Dako, Glostrup, Denmark), CD68 antibodies (1:100, Abcam, Cambridge, UK), and myeloperoxidase (MPO, 1:50, Abcam).

1-8. TUNEL Method

Terminal deoxynucleotidyl transferase dUTP nick end labeling (TUNEL) staining was applied using a DeadEnd Fluorometric TUNEL System kit (G3250; Promega, Medison, Wis.) in accordance with the manufacturer's protocol so as to detect dead cells on the lung sections. Subsequently, after nuclear counter-staining with DAPI, the number of TUNEL-positive cells was counted in six non-overlapping fields of the lungs 200X magnified using a confocal laser scanning microscope (LSM 700, ZEISS, Oberkochen, Germany).

1-9. Statistical Analysis

One-way ANOVA followed by Tukey-Kramer post hoc test was performed for multiple comparison, and all statistical analyses were performed using GraphPad Prism 5 (Graphpad Software, Inc., San Diego, Calif., USA). In addition, data was expressed as mean±SEM, and a P-value of less than 0.05 was considered statistically significant.

Example 2

Verification of Angiogenic Effect of WKYMVm on HUVECs

To investigate whether WKYMVm (SEQ ID NO: 1) contributes to angiogenesis by directly acting on endothelial cells, cell proliferation and vascular tube formation between WKYMVm (SEQ ID NO: 1)-treated groups and a non-treated group of HUVECs were compared with one another (see FIG. 1).

Figure 1B:
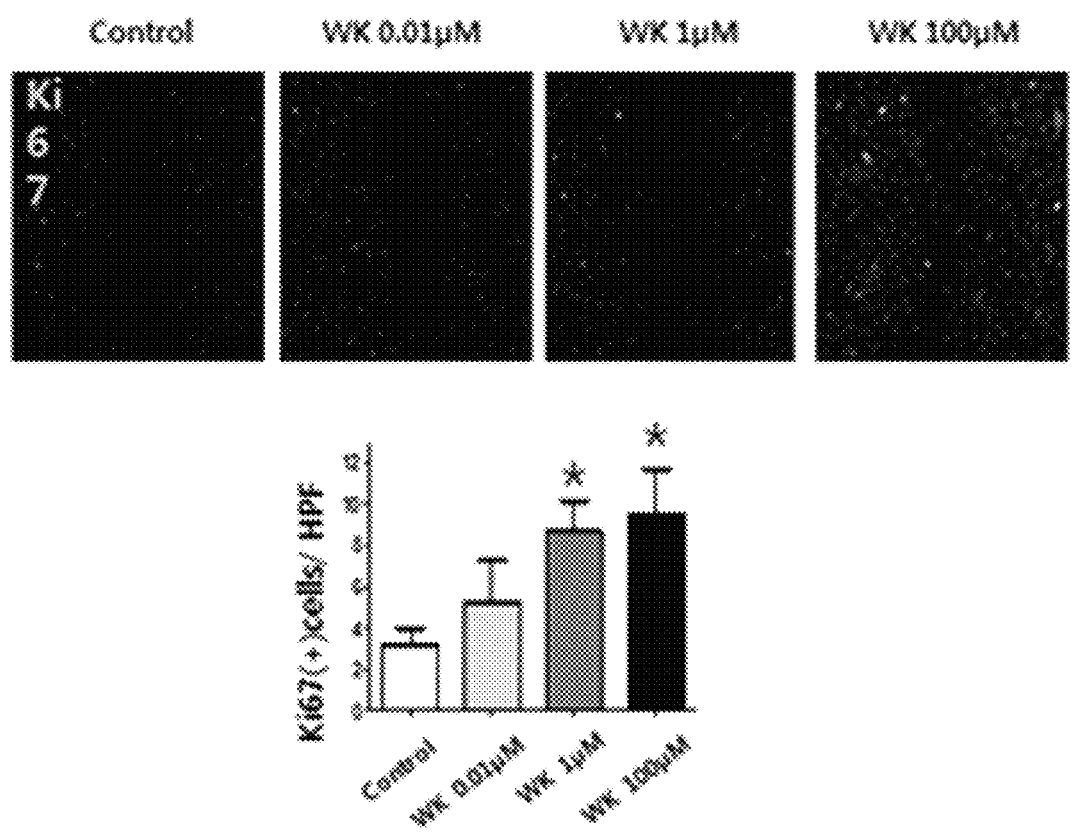
FIG. 1B illustrates results of determining the number of Ki67-positive cells in an experiment performed in series with the experiment of FIG. 1A.

As a result, as illustrated in FIGS. 1A and 1B, WKYMVm dose-dependently increased cell proliferation in the scratched areas of HUVEC monolayers, and this was further confirmed through the number of Ki67-positive cells. In this case, it was confirmed that the groups treated with WKYMVm (SEQ ID NO: 1) at concentrations of 1 μM and 100 μM exhibited significantly increased cell proliferation, whereas the group treated with WKYMVm (SEQ ID NO: 1) at a concentration of 0.01 μM did not exhibit significantly increased cell proliferation, as compared to the control.

Figure 1C:
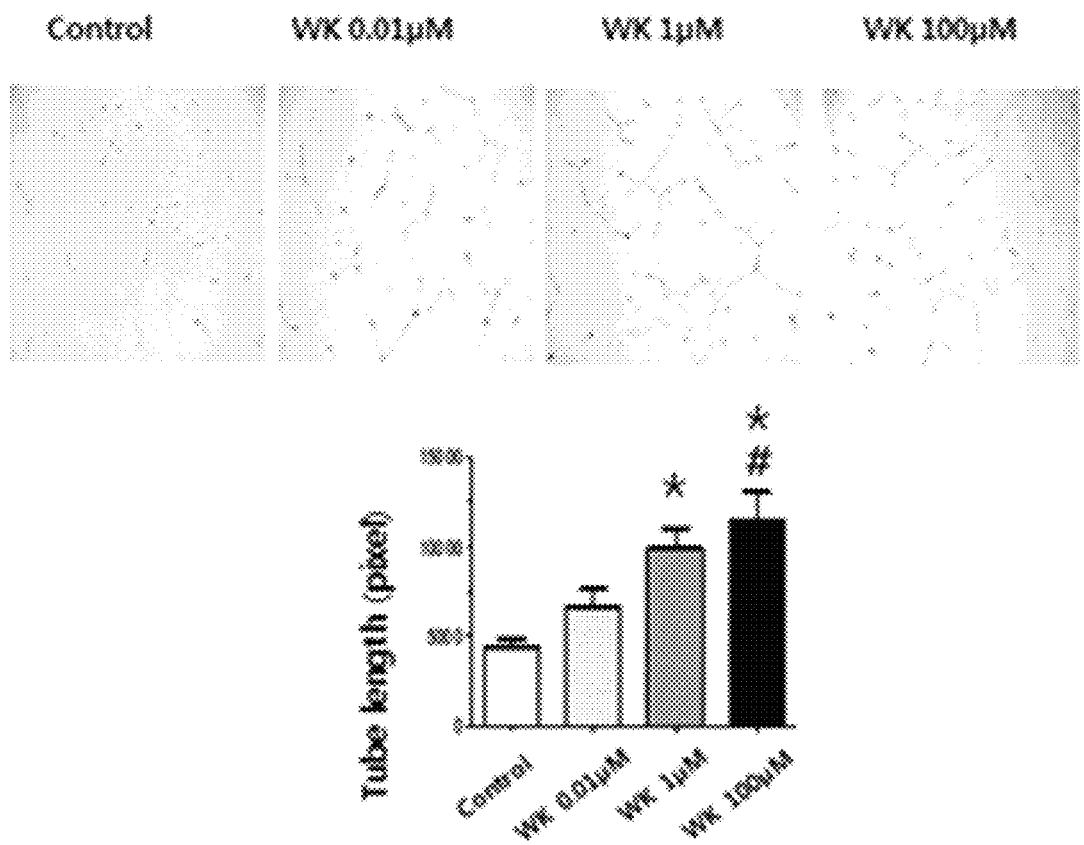
FIG. 1C illustrates results of analyzing HUVEC tube formation after WKYMVm treatment.

In addition, as illustrated in FIG. 1C, it was specifically confirmed that WKYMVm (SEQ ID NO: 1) significantly increased the vascular tube formation of HUVECs. In this case, it was confirmed that the groups treated with WKYMVm (SEQ ID NO: 1) at concentrations of 1 μM and 100 μM showed a significant increase in vascular tube length as compared to the control, and the tube length of the group treated with 100 μM of WKYMVm (SEQ ID NO: 1) was significantly greater than that of the group treated with 0.1 μM of WKYMVm (SEQ ID NO: 1).

Example 3

Verification of ERK Activation by WKYMVm in HUVECs

To confirm whether the cell proliferation increased by WKYMVm (SEQ ID NO: 1) treatment is dependent on the ERK pathway, levels of total ERK and phosphorylated (p) ERK were quantified by western blotting.

Figure 2A:
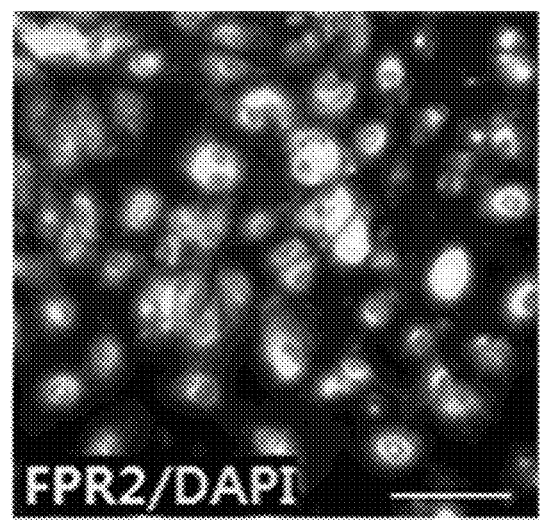
FIG. 2A illustrates a representative microscopic image of FPR2 immunostained in the HUVECs.
Figure 2B:
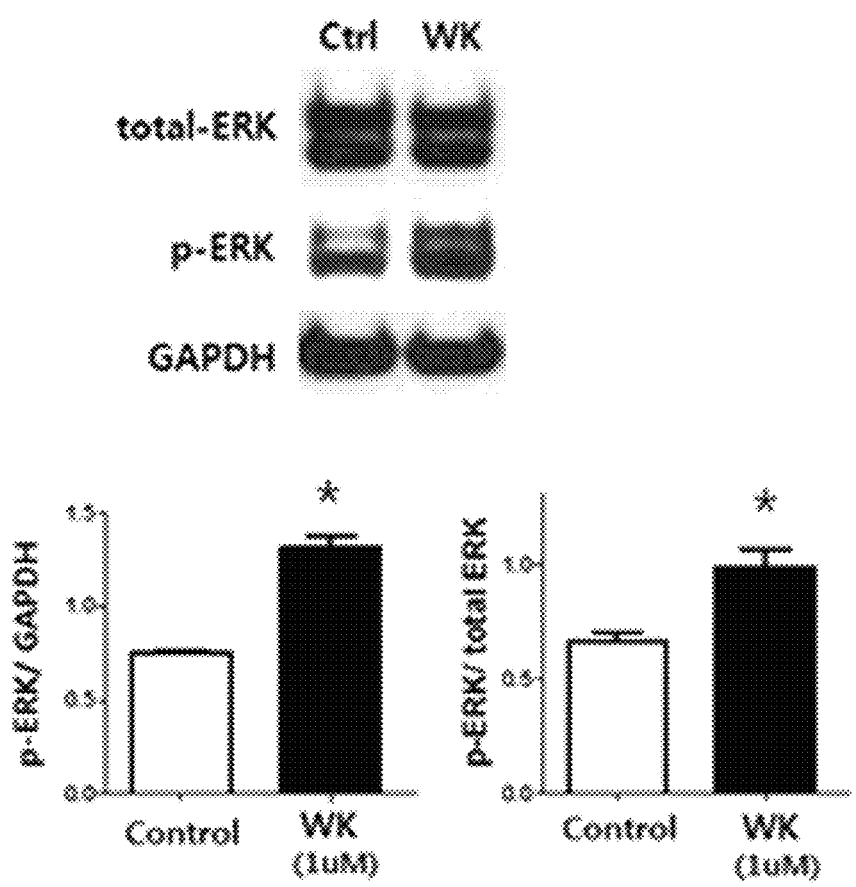
FIG. 2B illustrates representative western blotting results obtained by normalizing the concentration data of total ERK and p-ERK, and p-ERK and p-ERK/total ERK, with GAPDH.

As a result, as illustrated in FIG. 2A, it was specifically confirmed that the expression of FPR2 (green) in HUVECs was a result of WKYMVm (SEQ ID NO: 1) treatment, and as illustrated in FIG. 2B, it was confirmed that the levels of total ERK were almost similar to each other before and after WKYMVm (SEQ ID NO: 1) treatment, whereas the levels of p-ERK and p-ERK/total ERK were significantly higher in a WKYMVm (SEQ ID NO: 1)-treated group (WK) than in a control (Ctrl).

Example 4

In Vivo Verification of FPR2 Expression and ERK Activation by WKYMVm

Figure 3:
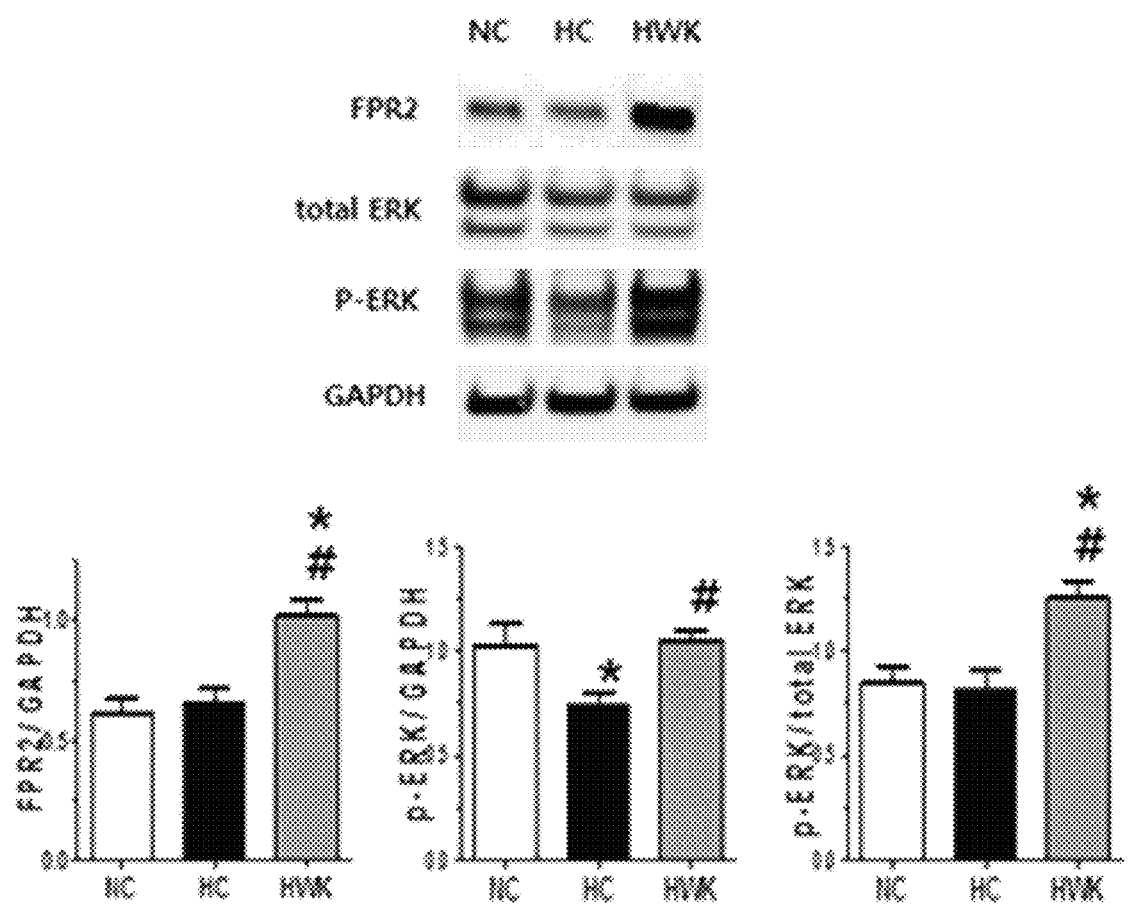
FIG. 3 illustrates western blotting results of the levels of FPR2 and p-ERK in the lungs of mice.

In the present disclosure, as a result of in vivo examination of FPR2 expression and ERK activation by WKYMVm (SEQ ID NO: 1), as illustrated in FIG. 3, it was confirmed that FPR2 expression was significantly increased in neonatal mouse lungs after WKYMVm (SEQ ID NO: 1) treatment.

In addition, it was confirmed that the level of p-ERK was significantly decreased in hyperoxia control (HC) lungs as compared to normoxia control (NC) lungs, whereas the level of p-ERK was significantly increased after WKYMVm (SEQ ID NO: 1) treatment, and it was also confirmed that a ratio of p-ERK to total ERK was significantly increased in HWK (hyperoxia with WKYMVm (SEQ ID NO: 1)) lungs as compared to the NC and HC lungs.

Example 5

Morphological Measurement of Alveolarization

Figure 4A:
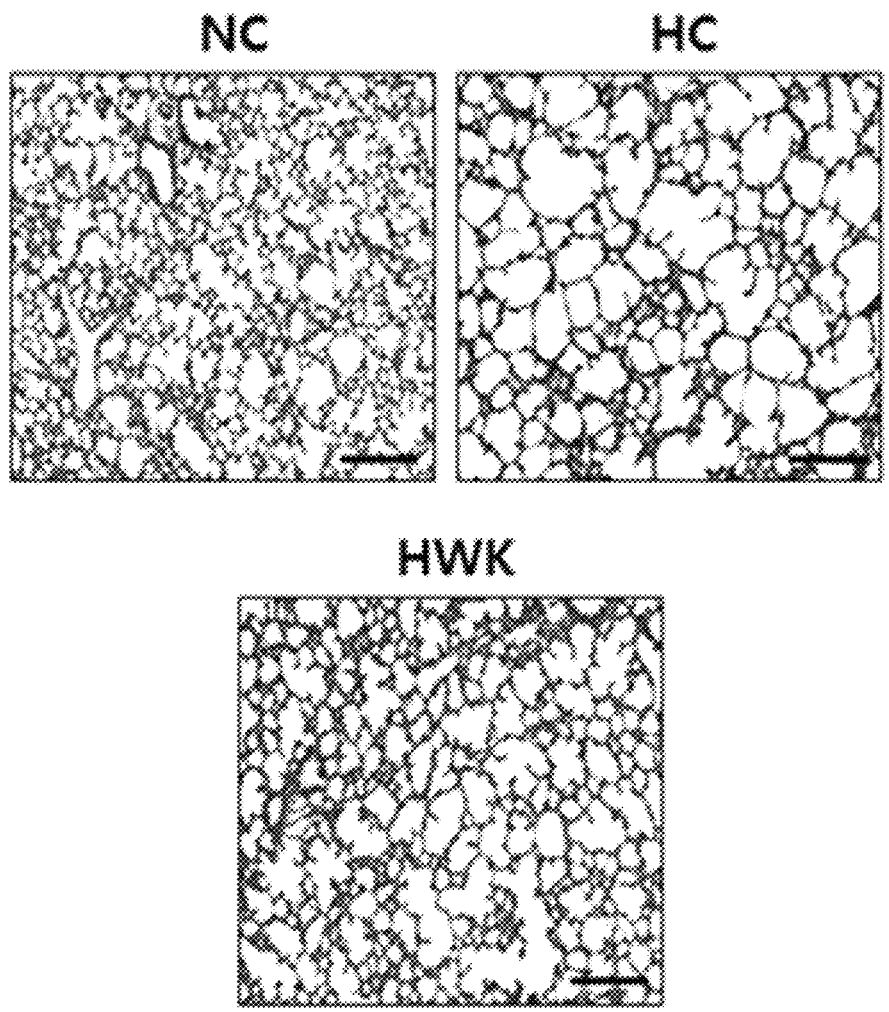
FIG. 4A illustrates histological and morphological evaluation results of alveoli in the lungs of mice, showing representative microscopic images of the lungs of mice stained with hematoxylin & eosin.
Figure 4B:
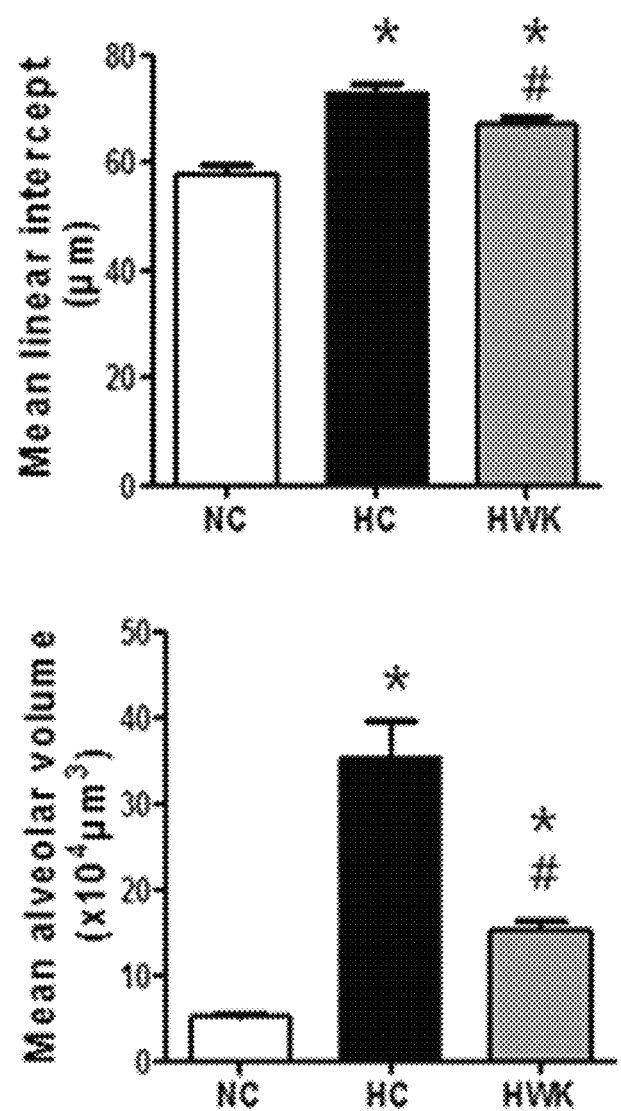
FIG. 4B illustrates histological and morphological evaluation results of alveoli in the lungs of mice, showing morphological evaluation results such as mean linear intercept (MLI) and mean alveolar volume (MAV)

A representative H&E-stained section for each experimental group is illustrated in FIG. 4A, and MLI and MAV, which respectively represent morphological data such as alveolar size and volume, are illustrated in FIG. 4B.

More particularly, as illustrated in FIG. 4A, hyperoxia-induced lung injury is characterized by heterogeneous and inflated alveoli, which are histological features exhibited with an increase in MLI and MAV, and as illustrated in FIG. 4B, it was confirmed that, whereas the MLI and MAV of HC were significantly increased compared to those of NC, those of HWK were significantly improved. In other words, it was confirmed that WKYMVm significantly suppressed hyperoxia-induced morphological damage in alveoli.

Example 6

Histological Evaluation of Angiogenesis, Apoptosis, and Inflammation

To confirm an effect of WKYMVm (SEQ ID NO: 1) treatment on angiogenesis, apoptosis, and inflammation in animal models, cell detection was performed using the vWF and TUNEL methods according to Examples 1-7 and 1-8.

Figure 5A:
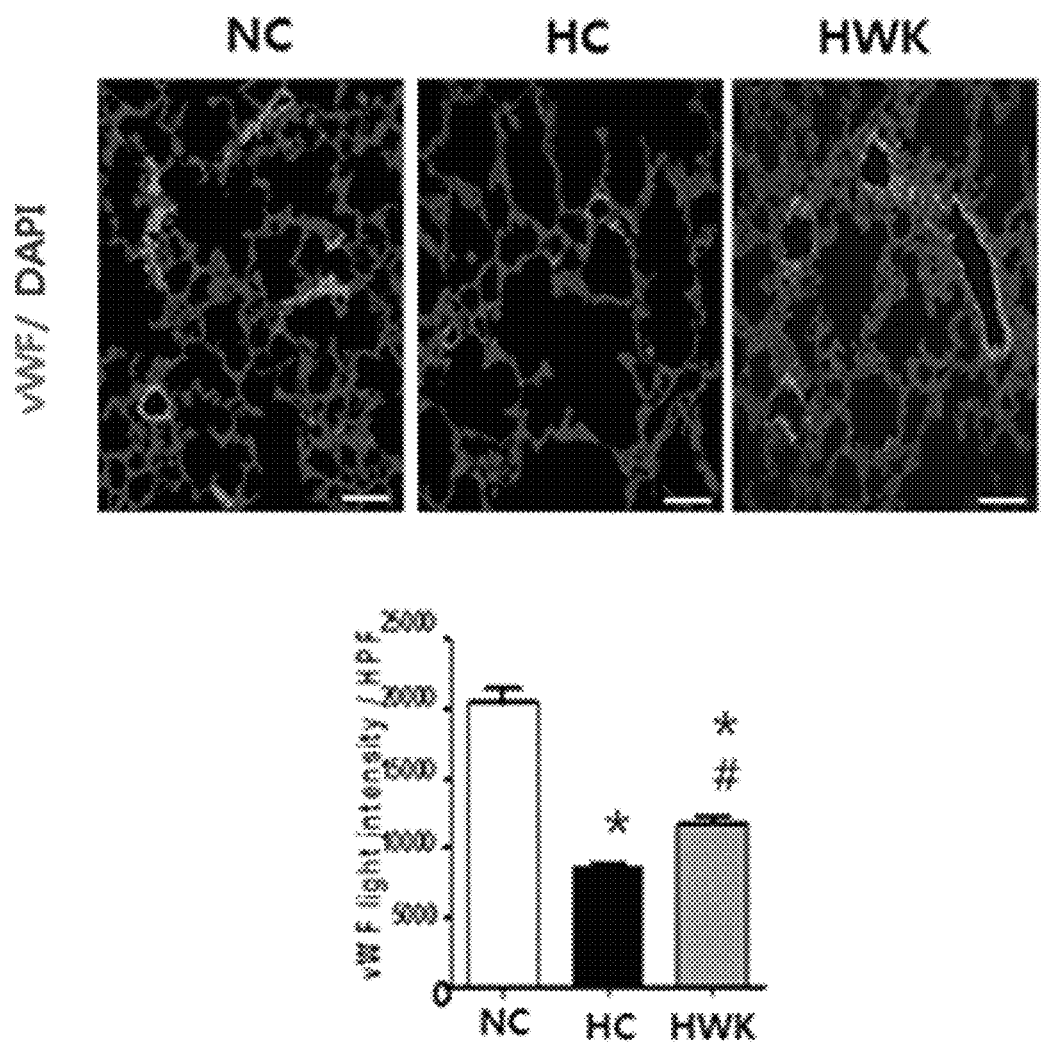
FIG. 5A illustrates histological analysis and evaluation results of angiogenesis and apoptosis in the lungs of mice, showing representative microscopic images of a von Willebrand factor (vWF) (red) and quantitative data of vWF intensity measurement.

As a result, as illustrated in FIG. 5A, it was confirmed that hyperoxia significantly reduced vWF (a marker for nascent endothelial cells) in the lungs being developed, and the intensity of vWF was significantly reduced in HC lungs as compared to in NC lungs, whereas the reduced vWF intensity was significantly increased in HWK lungs as compared to the HC lungs.

Figure 5B:
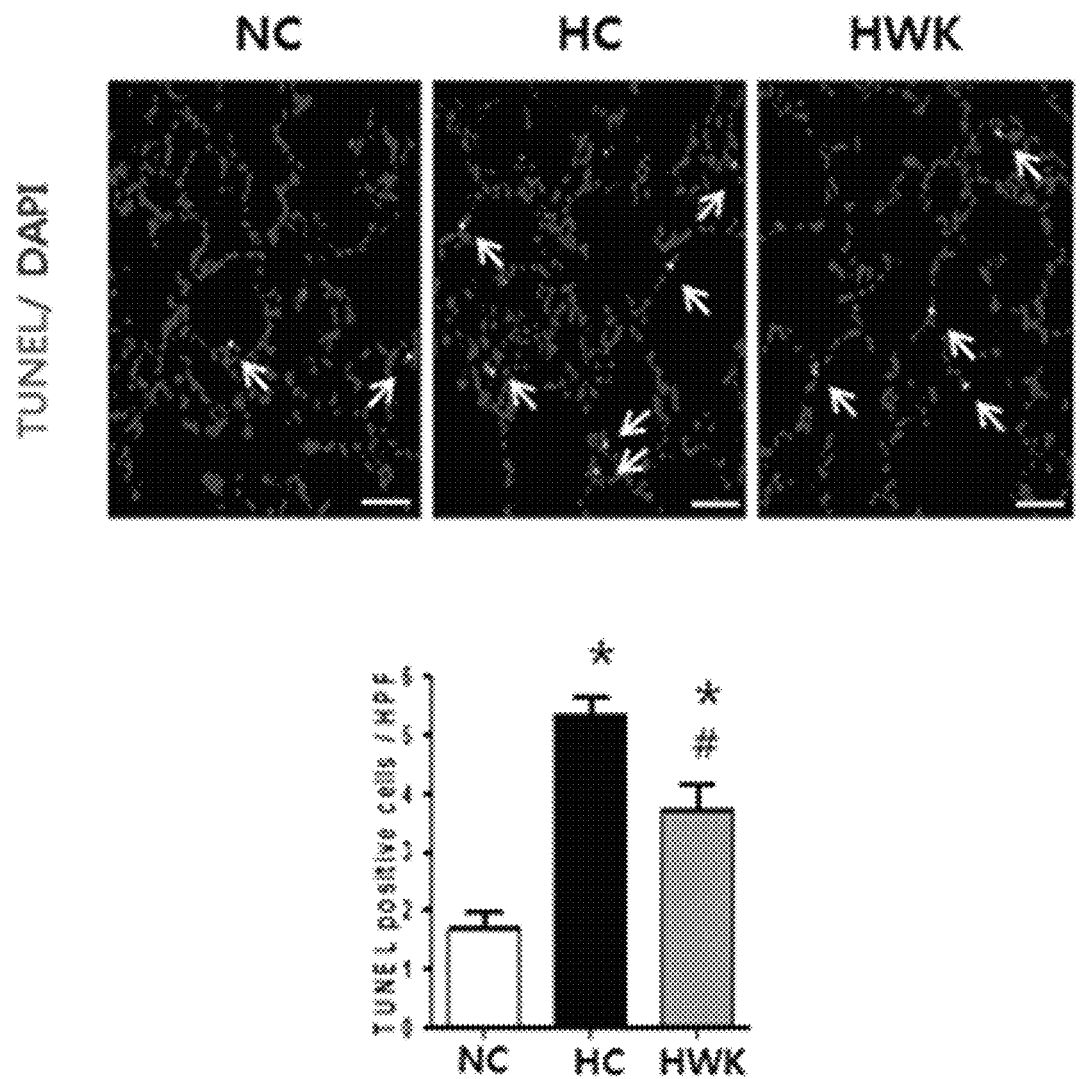
FIG. 5B illustrates histological analysis and evaluation results of angiogenesis and apoptosis in the lungs of mice, showing representative microscopic images of TUNEL (green) and quantitative data of TUNEL-positive cells.

In addition, increased apoptosis is another characteristic of hyperoxia-induced lung injury, and as illustrated in FIG. 5B, it was confirmed that after exposure to hyperoxia, the number of TUNEL-positive cells was significantly increased in HC as compared to NC, but the number of TUNEL-positive cells, which was increased in HC, was significantly reduced in HWK.

Figure 6A:
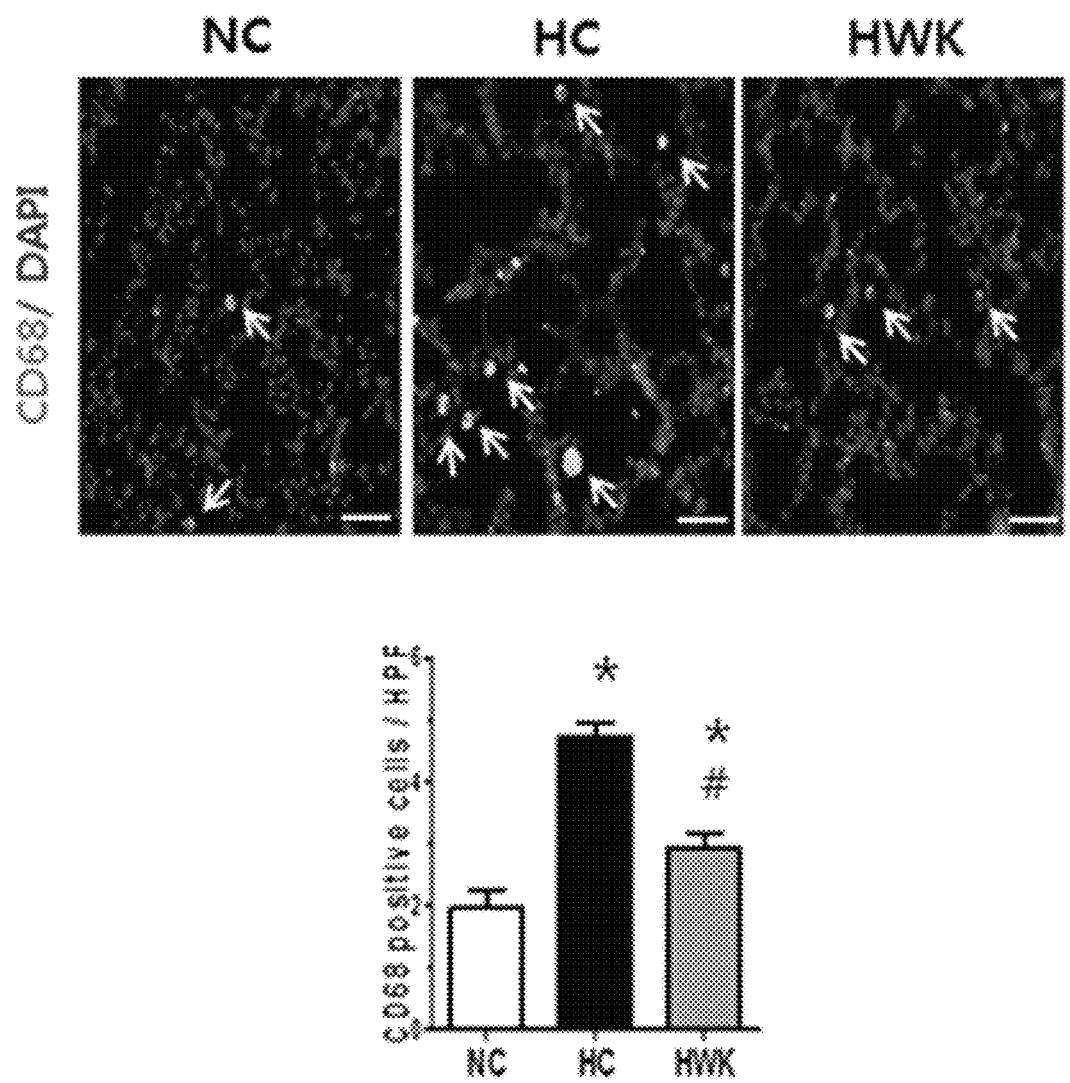
FIG. 6A illustrates histological analysis results of inflammatory cells infiltrated into the lungs of mice, showing representative microscopic images of CD68 (green) and quantitative data obtained by calculating the number of CD68-positive cells.
Figure 6B:
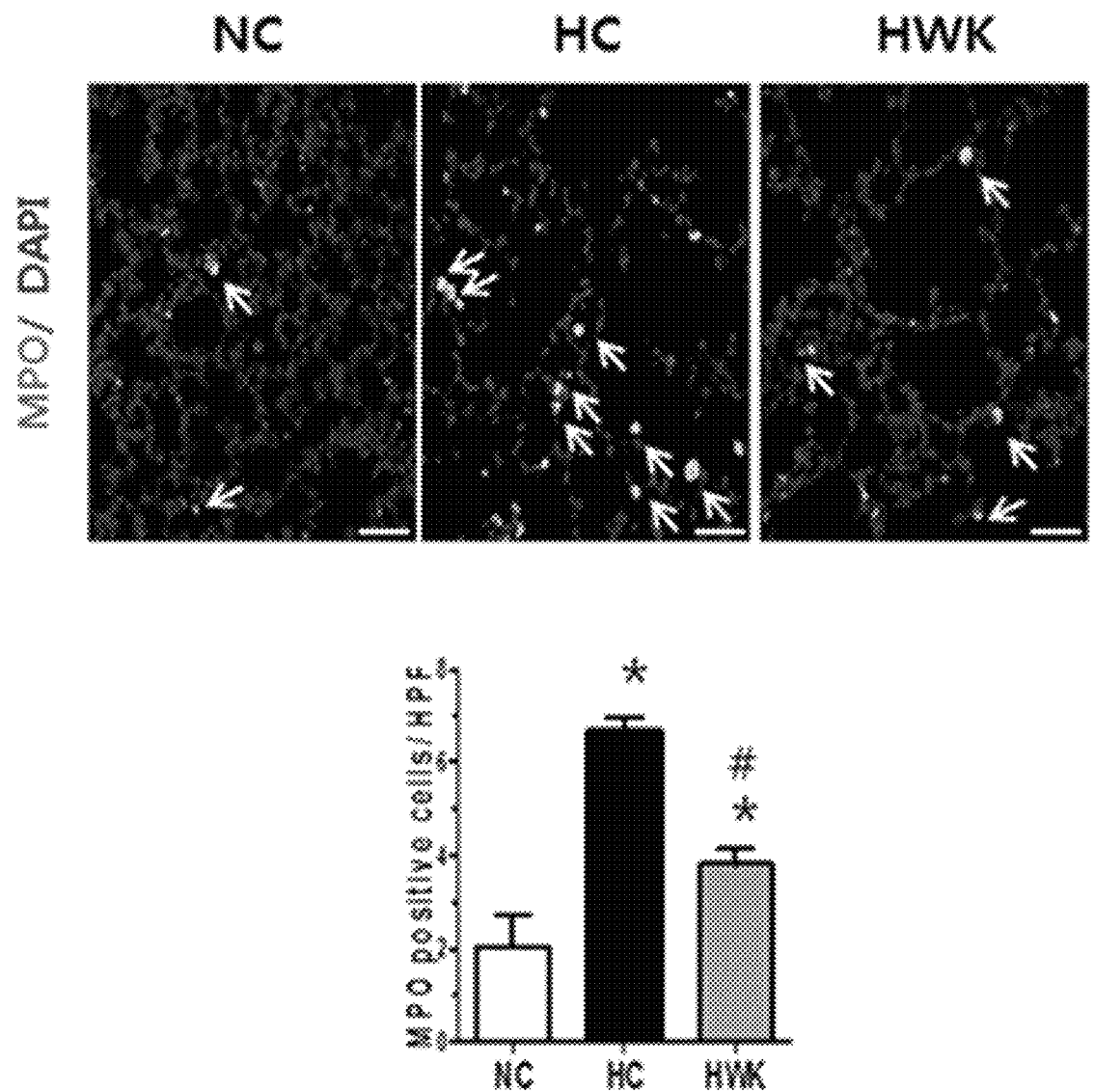
FIG. 6B illustrates histological analysis results of inflammatory cells infiltrated into the lungs of mice, showing representative microscopic images of myeloperoxidase (MPO) (green) and quantitative data obtained by calculating the number of MPO-positive cells.

In addition, as illustrated in FIGS. 6A and 6B, it was confirmed by macrophage marker CD68- and myeloperoxidase (MPO)-positive cells that lungs exposed to hyperoxia exhibited increased inflammation, and in this case, most MPOs were expressed by neutrophils, monocytes, and macrophages. However, it was specifically confirmed that the numbers of CD68- and MPO-positive cells, which were increased in HC, were significantly reduced in HWK.

As is apparent from the foregoing description, the WKYMVm (SEQ ID NO: 1) peptide has an effect of increasing FPR2 activation and ERK phosphorylation, and also has an effect of improving alveolarization and angiogenesis in hyperoxia-induced lung injury models. Thus, the WKYMVm (SEQ ID NO: 1) peptide is anticipated to be usefully used for the prevention or treatment of hyperoxia-induced lung injury, particularly bronchopulmonary dysplasia.

The foregoing description of the present disclosure is provided for illustrative purposes only, and it will be understood by those of ordinary skill in the art to which the present disclosure pertains that the present disclosure may be easily modified in other particular forms without changing the technical spirit or essential characteristics of the present disclosure. Thus, the above-described embodiments should be construed as being provided for illustrative purposes only and not for purposes of limitation.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A method of treating hyperoxia-induced lung injury comprising:
administering to a subject in need thereof an effective amount of a WKYMVm peptide, the WKYMVm peptide comprising the sequence of SEQ ID NO: 1,
wherein the hypoxia-induced lung injury is bronchopulmonary dysplasia, and
wherein the effective amount of the WKYMVm is from 1-100 µM.

2. The method of claim 1, wherein the WKYMVm peptide activates formyl-peptide receptor type 2 (FPR2).

3. The method of claim 1, wherein the WKYMVm peptide increases the phosphorylation of an extracellular signal-regulated kinase (ERK).

4. The method of claim 1, wherein the WKYMVm peptide induces angiogenesis.

5. The method of claim 1, wherein the WKYMVm peptide reduces inflammation.

6. A method of alleviating hyperoxia-induced lung injury comprising:
administering to a subject in need thereof an effective amount of a WKYMVm peptide to an individual, the WKYMVm peptide comprising the sequence of SEQ ID NO: 1,
wherein the hypoxia-induced lung injury is bronchopulmonary dysplasia, and
wherein the effective amount of the WKYMVm is from 1-100 µM.

7. The method of claim 6, wherein the WKYMVm peptide activates formyl-peptide receptor type 2 (FPR2).

8. The method of claim 6, wherein the WKYMVm peptide increases the phosphorylation of an extracellular signal-regulated kinase (ERK).

9. The method of claim 6, wherein the WKYMVm peptide induces angiogenesis.

10. The method of claim 6, wherein the WKYMVm peptide reduces inflammation.

* * * * *

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial
<220> FEATURE:
<223> OTHER INFORMATION: WKYMVm peptide
<220> FEATURE:
<221> NAME/KEY: MOD_RES
<222> LOCATION: (6)..(6)
<223> OTHER INFORMATION: D-Met

<400> SEQUENCE: 1

Trp Lys Tyr Met Val Met
1               5
```